(12) United States Patent
Vaillancourt et al.

(10) Patent No.: US 10,195,400 B2
(45) Date of Patent: Feb. 5, 2019

(54) DRESSSING

(71) Applicants: Michael J. Vaillancourt, Chester, NJ (US); Marshall Kerr, Carlsbad, CA (US)

(72) Inventors: Michael J. Vaillancourt, Chester, NJ (US); Marshall Kerr, Carlsbad, CA (US)

( * ) Notice: Subject to any disclaimer, the term of this patent is extended or adjusted under 35 U.S.C. 154(b) by 3 days.

(21) Appl. No.: 15/049,548

(22) Filed: Feb. 22, 2016

(65) Prior Publication Data

US 2016/0243338 A1 Aug. 25, 2016

Related U.S. Application Data

(63) Continuation-in-part of application No. 14/628,988, filed on Feb. 23, 2015.

(51) Int. Cl.
*A61M 5/32* (2006.01)
*A61M 25/02* (2006.01)

(52) U.S. Cl.
CPC ....... *A61M 25/02* (2013.01); *A61M 2025/024* (2013.01); *A61M 2025/028* (2013.01); *A61M 2025/0246* (2013.01); *A61M 2025/0253* (2013.01); *A61M 2025/0266* (2013.01); *A61M 2025/0273* (2013.01)

(58) Field of Classification Search
CPC .......... A61F 13/023; A61F 2013/00412; A61F 2013/00421; A61M 2025/0246; A61M 25/02
USPC ........................................ 604/180, 177, 174
See application file for complete search history.

(56) References Cited

U.S. PATENT DOCUMENTS

| 4,221,215 | A | * | 9/1980 | Mandelbaum | ...... | A61M 16/047 128/DIG. 26 |
|---|---|---|---|---|---|---|
| 4,633,863 | A | * | 1/1987 | Filips | ..................... | A61M 25/02 128/846 |
| 6,273,873 | B1 | * | 8/2001 | Fleischer | ............... | A61M 25/02 604/1 |
| 2007/0043326 | A1 | * | 2/2007 | Navarro | ................. | A61M 25/02 604/264 |
| 2007/0055205 | A1 | * | 3/2007 | Wright | .................. | A61F 13/023 604/174 |

\* cited by examiner

*Primary Examiner* — Phillip Gray
(74) *Attorney, Agent, or Firm* — Francis C. Hano; Carella, Byrne ErAc

(57) ABSTRACT

The dressing has a pad for adhesive securement to a patient that includes a bubble for covering over a housing of a Huber needle assembly embedded in the patient. A slit is formed in the pad to allow passage of the tubing of the Huber needle assembly. In one embodiment, an insert of foam material is provided in the bubble to rigidify the bubble. A second section may also be provided for folding over the pad to encase the tubing, catheter and clamp of the Huber needle assembly.

17 Claims, 7 Drawing Sheets

DRESSSING

This application is a Continuation-in-Part of application Ser. No. 14/628,988, filed Feb. 23, 2015.

This invention relates to a dressing. More particularly, this invention relates to a dressing for a Huber needle assembly.

As is known, for example from U.S. Pat. No. 8,574,197, vascular access devices (infusion ports) are embedded in patients to provide pain drugs, chemotherapy, antibiotics, antiviral or antifungal drugs as well as for hydration and nutrition. In addition, Huber needles are used to gain access to these devices. The typical Huber needle is constructed with a housing that can be manually gripped for manipulation by a practitioner, with an angled L-shaped needle that can be embedded within a patient.

A Huber needle assembly generally consists of an L-shaped Huber needle, a tubing that extends from the housing and that is in communication with the needle to convey a medicament or other fluid via the needle into the infusion port, a catheter on the end of the tube and a closure clamp positioned on an intermediate section of the tube.

Huber needles are commonly used for long term infusion therapy. The angle relationship of the needle allows the aft end of the needle to be safely anchored by being taped to the exterior surface of the skin of the patient in the area surrounding the infusion port.

Because a Huber needle may be left in place in a patient for several days, there is a need to cover the site where the needle is implanted into a patient.

Accordingly, it is an object of the invention to provide a relatively simple dressing for an implanted Huber needle.

It is another object of the invention to provide a dressing for an implanted Huber needle that can keep the site of the implanted needle in an antiseptic condition.

It is another object of the invention to provide a dressing for an implanted Huber needle assembly that protects the needle from inadvertent impacts.

It is another object of the invention to provide a dressing that is able to cover an implanted Huber needle assembly.

Briefly, the invention provides a dressing for a Huber needle assembly that is to be used with a Huber needle remaining embedded in a patient.

In one embodiment, the dressing includes two sections that are folded over each other to protect the embedded housing of the Huber needle as well as a tubing and catheter extending from the housing. The dressing is secured to the patient about the site of the Huber needle and allows the patient to be ambulatory over a period of days while maintaining the entire Huber needle assembly in a protected manner.

The first section of the dressing includes a pad that has an aperture for receiving the housing of a Huber needle that is embedded in a patient and a transparent bubble that is secured to the pad in alignment with the aperture to contain the housing of the Huber needle therein. In addition, the pad includes a slit for passage of the tubing from the housing of the Huber needle to allow the tubing, catheter and closure clamp to be wound about the bubble and lay flat against the topside of the pad. In like manner, the bubble is provided with a slit for passage of the tubing.

The pad is provided with a layer of adhesive on an underside for securing to the skin of a patient as well as three release layers over the adhesive to protect against inadvertent adherence of the pad to unintended objects prior to use.

The second section of the dressing is transparent and is sized to cover the first section and has an adhesive on a periphery for adherence to a patient. This second section sandwiches the wound tubing and catheter in place while encasing the Huber needle housing, tubing, catheter and closure clamp in a sterile manner. A release layer is also provided over the adhesive on the perimeter of the section to protect against inadvertent adherence of the section to unintended objects prior to use.

In this embodiment, the first section of the dressing includes an insert of rigid foam material that is disposed circumferentially within the bubble for cushioning the bubble against impact forces. The insert also protects against inadvertent impacts against the housing of the Huber needle. The insert may also have an antimicrobial agent on a bottom surface that contacts a patient.

In use, in order to encase a Huber needle assembly with a needle embedded in a patient, a first release layer is removed from a main section of the underside of the pad of the dressing to expose a layer of adhesive thereon and the pad applied against the skin of the patient in a manner so that the housing of the Huber needle is contained within the bubble on the pad. At the same time, the tubing of the Huber needle is passed through the slit in the pad and a slit in the bubble.

Next, the tubing with the catheter and closure clamp thereon is wound about the bubble. This is followed by folding the second section over and onto the pad to sandwich the tubing, catheter and clamp between the two sections while also covering the bubble. At the same time, the release layer on the second section is removed from the perimeter of the section to expose the adhesive for securement to the skin of the patient peripherally about the pad as well as to the periphery of the pad to encase the entire Huber needle assembly in a sterile environment.

As an alternative to using adhesives to secure the two sections of the dressing together, use may be made of a Zip-lock closure or a Velcro® closure.

In the case of a Zip-lock closure, one section of the dressing is made of an injection molded pad with an integral female component of the closure disposed in a U-shaped pattern inwardly spaced from the periphery of the pad. The other section of the dressing is made of an injection molded film with an integral male component of the closure disposed in a U-shaped pattern inwardly spaced from the periphery of the film. When the two sections of the dressing are pressed together, the male component mates with the female component to provide a sealed securement of the two sections together.

In another embodiment, the dressing is formed by the first section alone. In this embodiment, the second section is removed or not secured to the first section in the first place. When placed into use to encase an implanted Huber needle assembly in a patient, the pad of the dressing is applied against the skin of the patient to contain the housing of the Huber needle within the bubble on the pad and the tubing of the Huber needle is passed through the slit in the pad and the slit in the bubble. Thereafter, the tubing, catheter and closure clamp of the Huber needle need not be covered over but may lay exposed.

These and other objects of the invention will become more apparent from the following detailed description taken in conjunction with the accompanying drawings in which.

Figure 12:
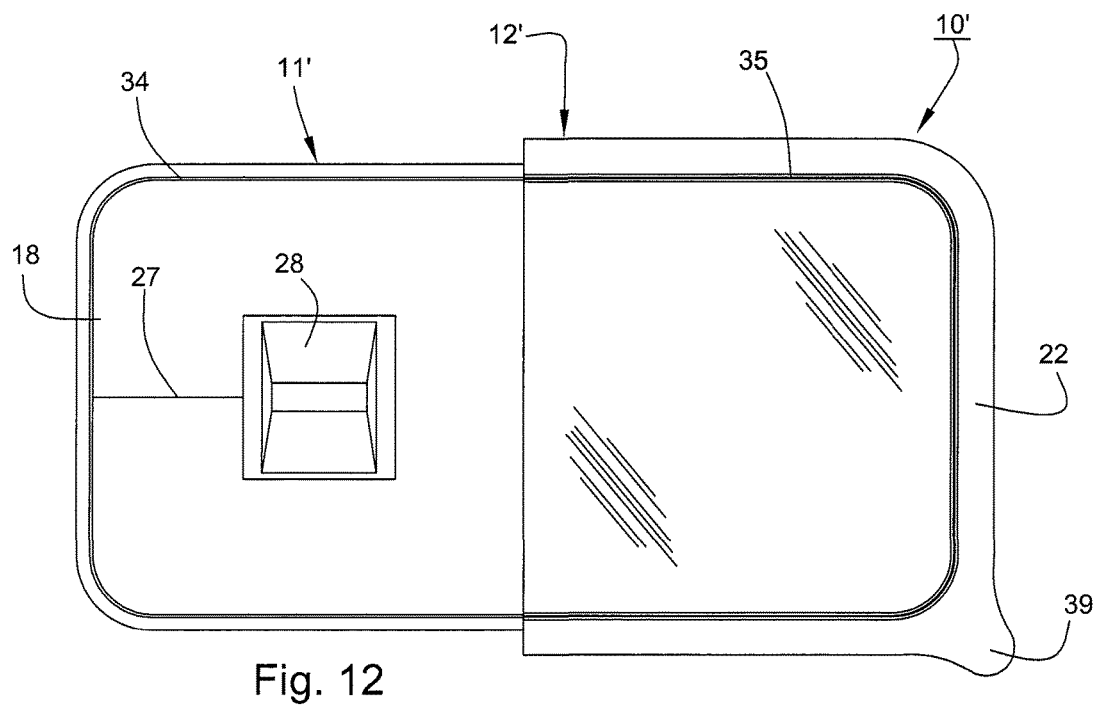
FIG. 12 illustrates a top view of a modified dressing with a Zip-lock type closure in accordance with the invention.
Figure 13:
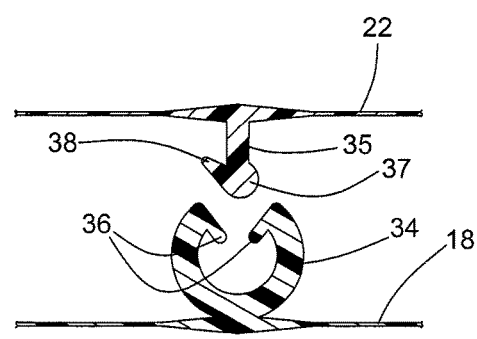
Figure 14:
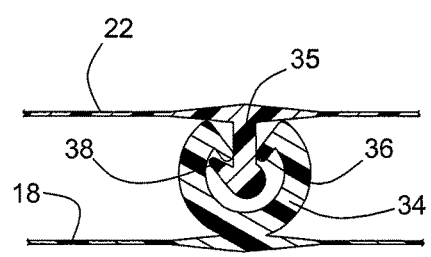

FIG. 13 schematically illustrates a cross-sectional view of the components of the Zip-lock type closure of FIG. 12 in an opened condition; and FIG. 14 schematically illustrates a cross-sectional view of the components of the Zip-lock type closure of FIG. 12 in a closed condition.

Figure 1:
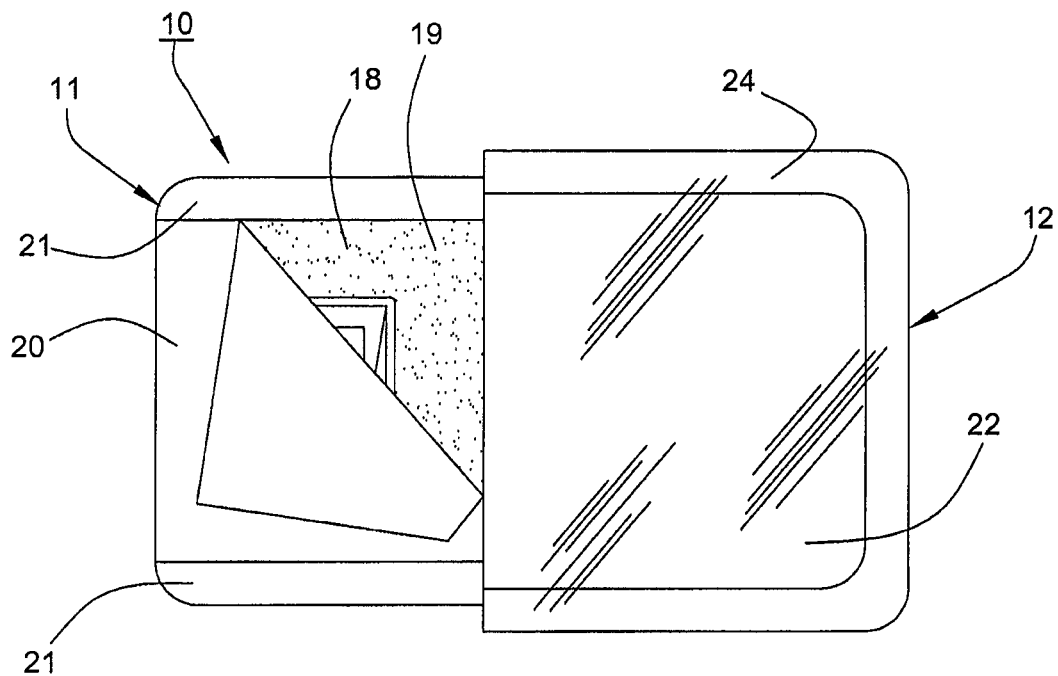
FIG. 1 illustrates a bottom view of a dressing constructed in accordance with the invention.

Referring to FIG. 1, the dressing 10 includes two sections 11, 12 that are to be folded over each other when in use to protect the site of an implanted Huber needle assembly.

Figure 3:
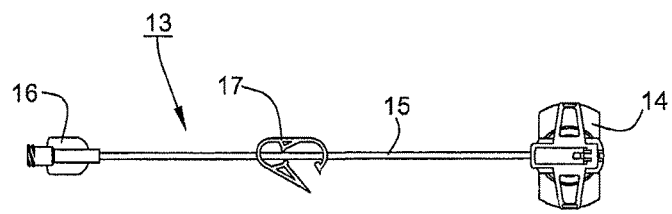
FIG. 3 illustrates a top view of a Huber needle assembly for which the dressing of FIG. 1 is employed.

Referring to FIG. 3, the Huber needle assembly 13 includes a housing 14 for an L-shaped Huber needle (not shown), a tubing 15 that extends from the housing 14 and that is in communication with the needle to convey a medicament or other fluid via the needle into an infusion port within a patient (not shown), a catheter 16 in the form of a female luer on the end of the tubing 15 and a closure clamp 17 positioned on an intermediate section of the tubing 15.

Referring to FIG. 1, the first section 11 of the dressing 10 includes a pad 18 of rectangular shape that is provided with an adhesive layer 19 suitable for adhering to the skin of a patient. In addition, the adhesive layer 19 is covered by a main removable release layer 20 and two side strip-like removable release layers 21.

The pad 18 is made of a polyethylene material, such as a 3M #1772 Medical Tape, as is known in the industry.

The second section 12 of the dressing 10 is of rectangular shape and is made of a thin transparent plastic film 22, for example of polyethylene, that has a layer of adhesive 23 of a medical grade acrylic based adhesive on three peripheral sides (see FIG. 7) of the top surface for adherence to the pad 18 and a patient and a removable release layer 24 of Kraft liner on the periphery that covers the adhesive 23.

The two sections 11, 12 of the dressing 10 are secured to each other via a narrow lip 25 (see FIG. 9) that projects from one side of the plastic film 22 that is equal to the width of the pad 18 and that is adhered to the pad 18 via the adhesive layer 20, being sandwiched between the adhesive layer 20 and the release layers 21, 22.

Figure 2:
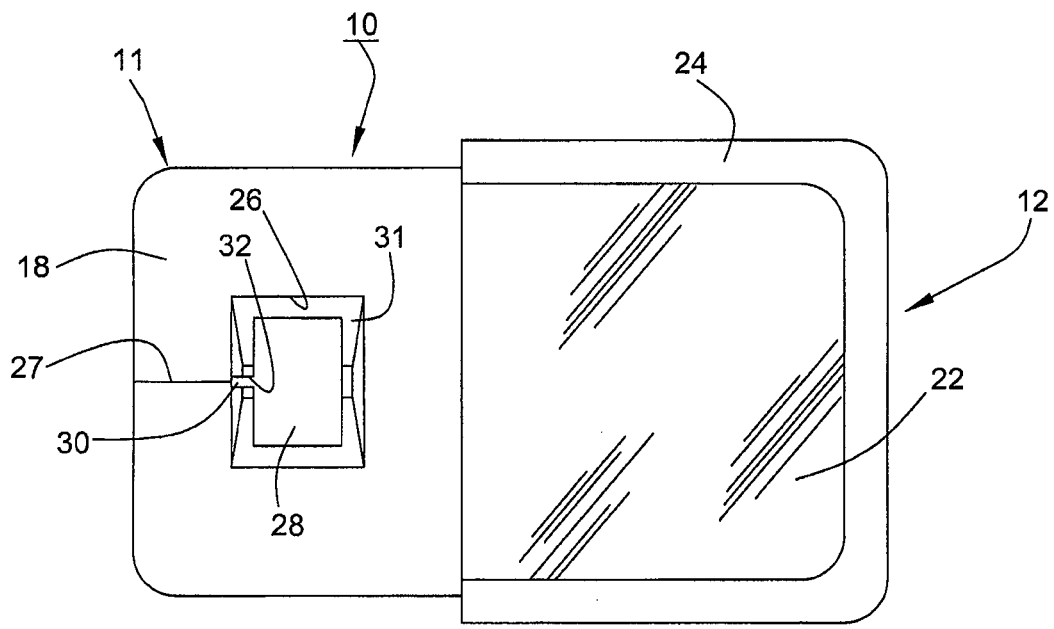
FIG. 2 illustrates a top view of the dressing of FIG. 1.

Referring to FIG. 2, the pad 18 has a centrally located aperture 26, for example of rectangular shape, and a slit 27 that extends from the aperture 26 to the edge of the pad 18.

Figure 9:
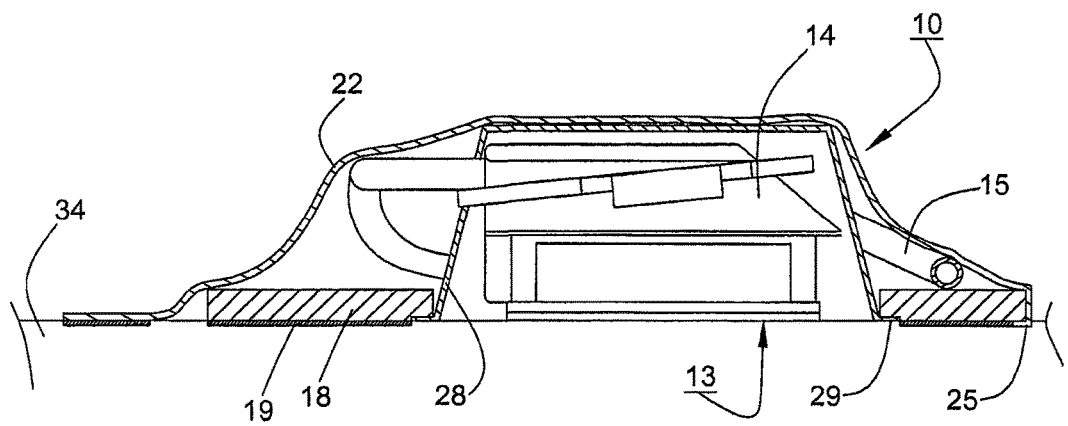
FIG. 9 illustrates a cross-sectional view taken on line 9-9 of FIG. 8.

In addition, a self-supporting bubble 28 of transparent plastic is mounted in the aperture 26 in mating relation and has a peripheral flange 29 that is adhered to the adhesive layer 20 on the underside of the pad 18 (see FIG. 9).

Referring to FIGS. 2 and 9, the bubble 28 is shaped to accommodate the shape of the housing 14 of the Huber needle assembly 13 and, for example, has a pyramidal shape with four sloped sides and a flattened top surface. In addition, the side of the bubble 28 facing the slit 27 has a slot 30 in alignment with the slit 27.

The bubble 28 may be also provided with a vent hole (not shown) for breathability. Likewise, the pad 18 and plastic film 23 are made of materials to be breathable thereby allowing air to reach the wound site of the Huber needle.

Referring to FIG. 2, in one embodiment, an insert 31 is optionally provided within the bubble 28 that is made of a rigid foam material and is disposed circumferentially within the bubble 28 for cushioning the bubble 28 against impact forces. As illustrated, the insert 31 is made of one piece with a slot 32 on one side for alignment with the slot 30 in the bubble 28 and the slit 27 in the pad 13.

Figure 4:
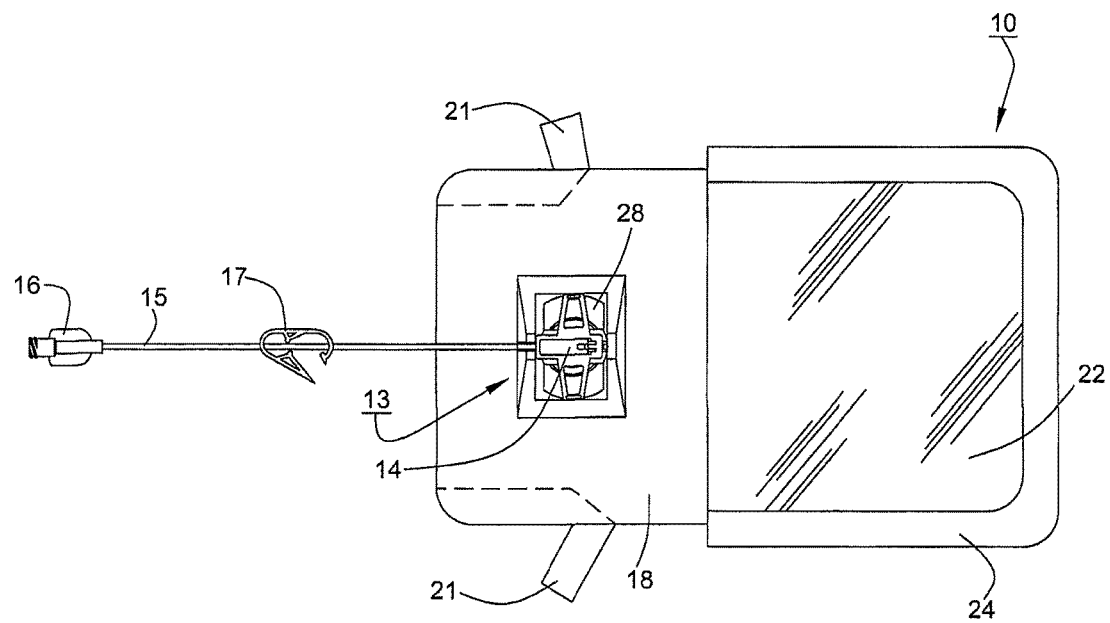
FIG. 4 illustrates a top view of the dressing of FIG. 1 with the pad-containing section positioned in place over a housing of a Huber needle assembly and the release layers on the side edges of the section in the process of being removed in accordance with the invention.

As illustrated in FIG. 4, when the dressing 10 is to be placed over an embedded Huber needle assembly 13, the main removable release layer 20 (not shown) on the pad 18 of the first section 11 is peeled away to expose the adhesive layer 19 and the practitioner manually grasps the two side edges of the pad 18 still covered by the two side strip-like removable release layers 21 to position the bubble 28 over the housing 14 of the Huber needle assembly 13. As the pad 18 is pressed against the skin of the patient, the remaining strip-like removable release layers 21 are peeled away as illustrated.

Figure 5:
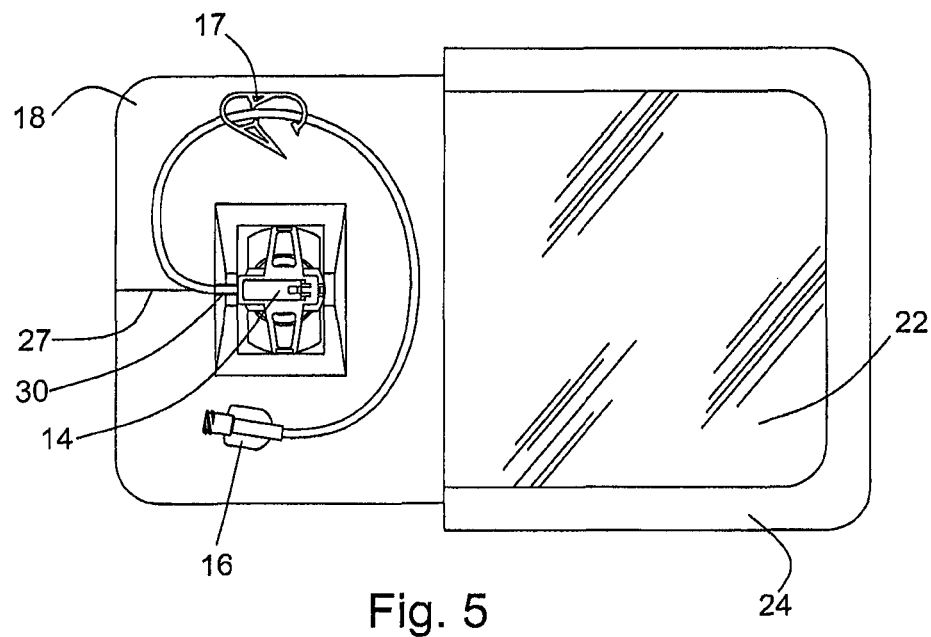
FIG. 5 illustrates a view similar to FIG. 4 with the tubing, catheter and clamp of the Huber needle assembly in the process of being wound about the bubble of the pad-containing section.

As the pad 18 of the first section 11 of the dressing 10 is being pressed into place, the tubing 15 of the Huber needle assembly 13 is passed through the slit 27 in the pad 18 and the slot 30 in the bubble 28 (See FIG. 5).

Referring to FIG. 5, after passage through the slit 27 in the pad 18, the tubing 15 of the Huber needle assembly 13 is wound about the bubble 28 and laid flat against the upper surface of the pad 18 along with the closure clamp 17 and catheter 16.

Figure 6:
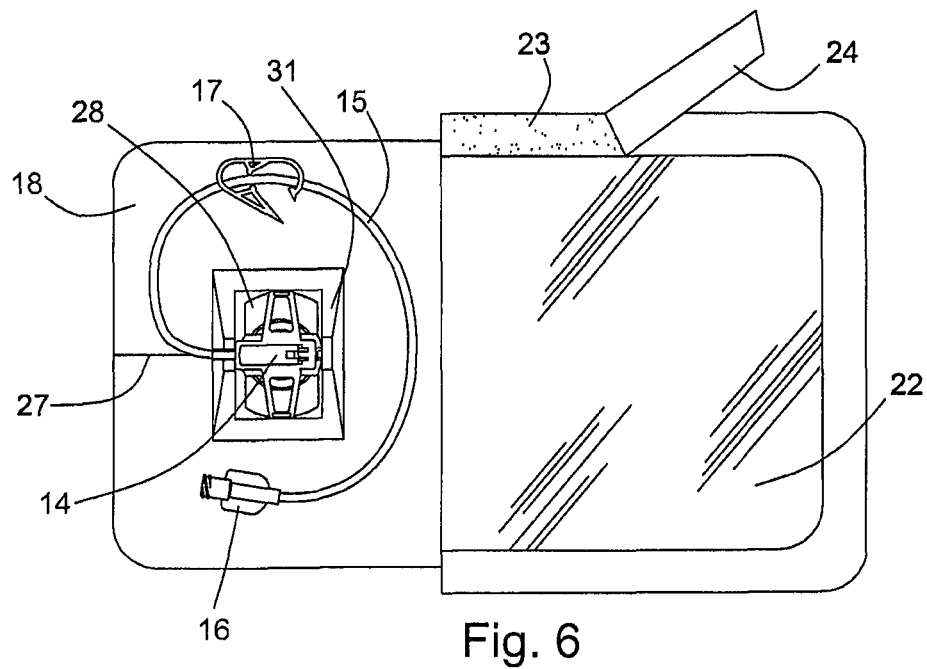
FIG. 6 illustrates a view similar to FIG. 5 with a release layer on the cover-forming section of the dressing in the process of being removed.
Figure 7:
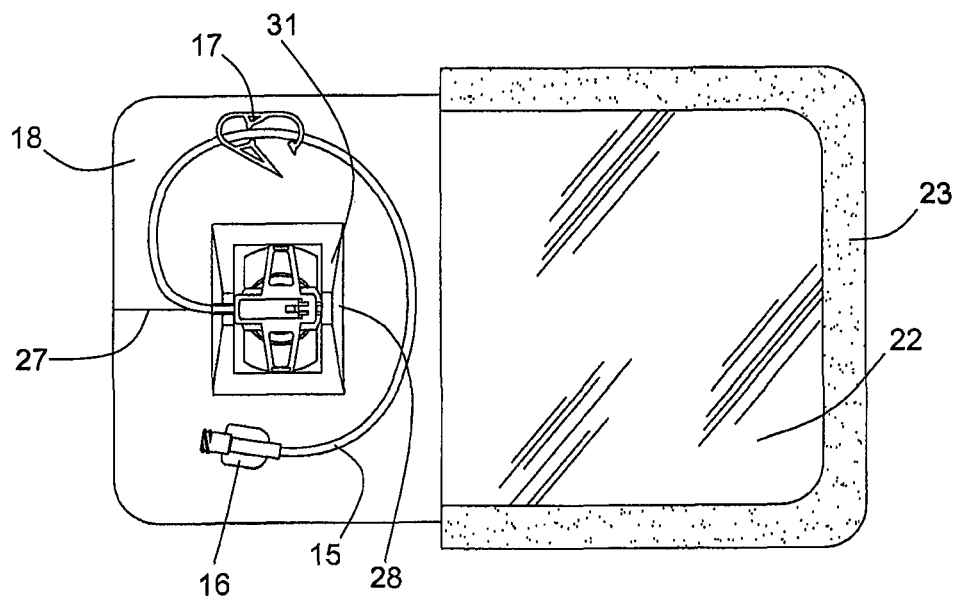
FIG. 7 illustrates a view similar to FIG. 5 with the release layer of the cover-forming section completely removed.

Next, referring to FIGS. 6 and 7, the release layer 24 on the plastic film 22 of the second section 12 of the dressing 10 is peeled away to expose the adhesive 23 on the three side edges of the plastic film 22. Thereafter, the plastic film 22, in the manner of a cover, is folded over the pad 18, bubble 28, wound tubing 15, closure clamp 17 and catheter 16. The periphery of the plastic film 22 is then pressed against the skin of the patient to adhere the plastic film 22 to the patient via the adhesive 23 and to encase the pad 18, tubing 15, clamp 17 and catheter 16 as illustrated in FIGS. 8 and 9.

Figure 8:
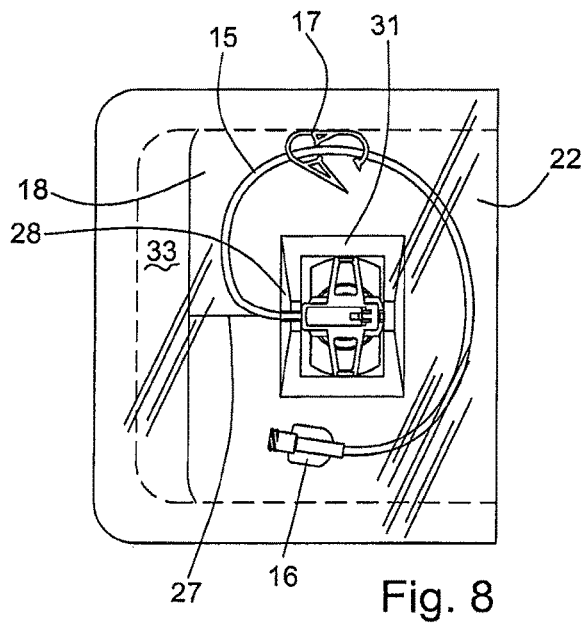
FIG. 8 illustrates a view of the dressing of FIG. 1 in a folded over condition over the Huber needle assembly in accordance with the invention.

As indicated in FIGS. 7 and 8, the width of the plastic film 22 is wider than the width of the pad 18 and the width of the adhesive 23 on the two lateral side edges of the plastic film 22 is sufficient to seal against and along the two lateral side edges of the pad 18 to seal off those lateral side edges from the surrounding environment. The length of the plastic film 22 is longer than the length of the pad 18 such that a gap 33 exists between the end edge of the pad 18 and the adhesive 23 on the end edge of the plastic film 22.

Of note, there are different types of Huber Needle line sets; some are short and some are long and contain Y-Site injection ports or needles connectors. The extra length of the plastic film 22 allows for coverage of multiple configurations. If the line set is longer and contains a swabable Y-Site, the gap 33 will not be there.

Referring to FIG. 9, when the dressing 10 is in place over the Huber needle assembly 13, the pad 18 is adhered to the skin of a patient 32 completely around the centrally located aperture 26 through which the bubble 28 is inserted in order to maintain the Huber needle site sterile. The plastic film 22 is adhered to the skin of the patient 34 on three sides and is integral with the pad 18 of the fourth side so as to encase the tubing 15, clamp 17 and catheter 16 in a closed chamber.

Figure 10:
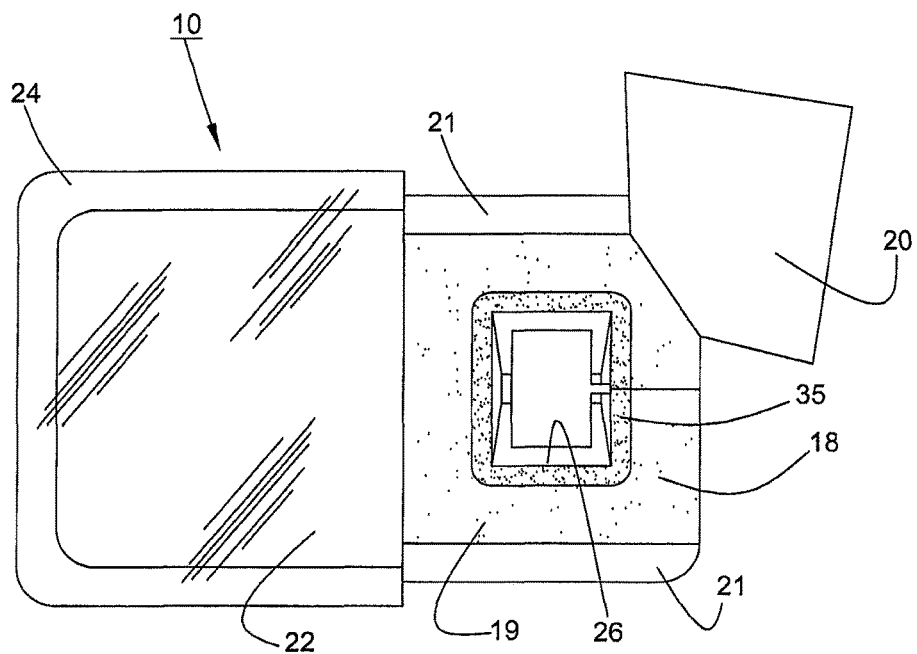
FIG. 10 illustrates a bottom view of a modified dressing with a microbial layer about the periphery of the bubble in the pad-containing section of the dressing.

Referring to FIG. 10, wherein like reference characters indicate like parts as above, bottom surface of the pad 18 may be provided with a microbial layer 35 about the periphery of the bubble-receiving aperture 26. The layer may be formed by a suitable thin antimicrobial material as is known in the art that is cut into a rectangular ring shape or other suitable shape.

Alternatively, the flange 29 of the bubble 28 may be provided with an antimicrobial coating to help fight infection.

Figure 11:
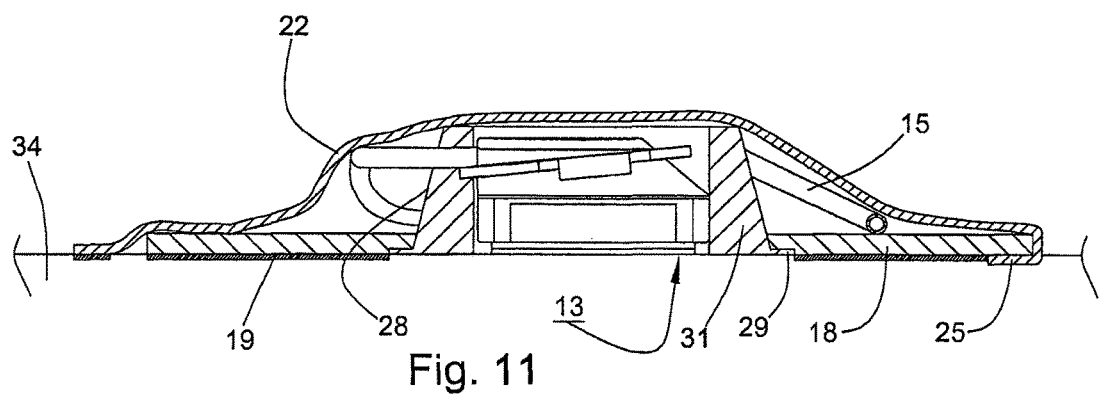
FIG. 11 illustrates a bottom view of a dressing having an insert of rigid foam material in the bubble of the pad-containing section in accordance with the invention.

Referring to FIG. 11, wherein like reference characters indicate like parts as above, where an insert 31 is optionally provided within the bubble 28, the insert 31 is made of one piece with the slot 32 on one side aligned with the slot 30 in the bubble 28. As illustrated, the insert 31 is of a rectangular ring shape and is sized to fit into the bubble 28 in a slide fit manner and to take on the shape of the interior surfaces of the walls of the bubble 28. The insert 31 is of a height equal to the inside height of the bubble 28 so as to rigidify the bubble 28 against inadvertent impacts.

In the embodiment where the insert 31 is not used, the bubble 28 may be made of a smaller size to fit snugly over the housing 14 of the Huber needle assembly 13.

Advantageously, the bubble 28 is transparent to allow the housing 14 of the Huber needle assembly 13 and the needle insertion site to be viewed for infection. Further, the pad 18 of the dressing functions as a comfort pad that prevents the closure clamp 17 and catheter 26 of the needle assembly from digging into the skin of a patient when the plastic film 22 is applied over the pad 18.

Where the plastic film 22 of the second section 12 of the dressing 10 is made of a stiff plastic, the plastic film 22 may form a dome-shaped cover over the bubble 28 thereby affording further protection against inadvertent impacts on the housing 14 of the Huber needle assembly 13. Where the plastic film 22 is made of a more flexible plastic, the film 22 may lie in a flattened manner over the bubble 28 or may conform to the bubble 28 and surrounding line set.

After being closed, the dressing 10 may be readily opened to allow a practioner or patient to gain access to the catheter 16 of an implanted Huber needle assembly 13 in order to administer a medicament or other fluid to the patient. Further, should the dressing 10 be used without closing the two sections 11, 12 onto each other, a patient may readily close the two sections 11, 12 together in order for the patient to take a shower without water and/or soap suds entering between the sections 11, 12.

Referring to FIG. 12, wherein like reference characters indicate like parts as above, the dressing 10' has two sections 11', 12' that are to be folded over each other, as above, when in use to protect the site of an implanted Huber needle assembly.

The first section 11' is made as above described with respect to FIGS. 1 and 2 including a slot (not shown) in the bubble 28 and a slit 27 in the pad 18.

Referring to FIGS. 12 and 14, the pad 18 of the first section 11' is injection molded with an integral female component 34 of a zip-lock type of closure that is disposed in a U-shaped pattern inwardly spaced from the periphery of the pad 18.

The second section 12' is made as above of a single ply film 22. Referring to FIGS. 12 and 13, the film 22 is an injection molded film with an integral male component 35 of the closure that is disposed in a U-shaped pattern inwardly spaced from the periphery of the film 22.

In this embodiment, the two sections 11', 12' are welded together along adjacent edges in a manner that allows the two sections 11', 12' be folded over each other.

As indicated in FIG. 14, when the two sections 11', 12' of the dressing 10' are pressed together, the male component 35 mates with the female component 34 to provide a sealed securement of the two sections 11', 12' together to keep moisture from entering between the two sections 11', 12'.

Referring to FIG. 13, the female component 34 of the closure has a circular cross-sectional shape with a pair of inwardly directed tabs 36 forming a slot in the component 34. The male component 35 has a cross-sectional pin shape with a bulbous end 37 formed with a projection 38 angled toward the film 22. In use, the male component 35 is pressed into the female component 34 such that the bulbous end 37 and projection 38 bias the tabs 36 of the female component apart to allow the projection 38 to engage under one of the tabs 36 as shown in FIG. 14.

While the closure 34, 35 is made in a continuous U-shaped manner with rounded corners to facilitate injection molding, the closure may also be made of three mutually perpendicular parts with a gap between adjacent parts. In this case, the film 22 may be provided with a bump (not shown) or the like to block the gap formed between two mutually perpendicular parts against entry of moisture.

As indicated in FIG. 12, the two sections 11', 12' of the dressing 10' are of the same width as the second section 12' does not require adhesion by adhesive to a patient. In addition, the components 34, 35 are line-to-line so that when the sections 11', 12' are folded over, the two sections 11', 12' will interlock via the components 34, 35. Also, the film 22 of the second section 12' will stretch slightly at the bend point about the edge of the pad 18.

As also indicated in FIG. 12, the film 22 may be formed with a projecting tab 39 to facilitate manual gripping of the section 12' for separating the two sections 11', 12' for separating the two sections 11', 12' after closure on each other.

The invention thus provides a relatively simple dressing for an implanted Huber needle assembly that can keep the site of the implanted needle in an antiseptic condition and that can effectively cover and contain the tubing, catheter and clamps of the needle assembly.

The invention also provides a dressing for an implanted Huber needle assembly that protects the needle from inadvertent impacts.

Still further, the invention provides a dressing that can remain in place for extended periods to allow a patient with a Huber needle in place to be ambulatory when not receiving an infusion fluid.

What is claimed is:
1. A dressing for a Huber needle assembly comprising
a pad having an aperture for receiving a housing of a Huber needle embedded in a patient and an adhesive on an underside of said pad for adhering to a patient;
a transparent bubble secured to said pad in alignment with said aperture to contain the housing of the Huber needle assembly therein and having a slot for passage of a tubing from the housing of the Huber needle assembly for winding about said bubble; and a section for folding over said pad and said bubble to cover said pad and said bubble with the tubing around said bubble, said section having an adhesive on a periphery thereof for adherence to a patient.

2. A dressing as set forth in claim 1 wherein said section is transparent.

3. A dressing as set forth in claim 1 wherein said section includes a removable release strip over said adhesive.

4. A dressing as set forth in claim 1 further comprising a closure for securing said section to said pad to keep moisture from entering between said section and said pad.

5. A dressing as set forth in claim 4 wherein said closure includes a female component on said pad disposed in a U-shaped pattern and a male component on said section disposed in a U-shaped pattern for mating with said female component.

6. A dressing as set forth in claim 1 wherein said pad includes a slit in alignment with said slot for passage of the tubing from the housing of the Huber needle assembly for winding about said bubble.

7. A dressing as set forth in claim 1 further comprising an insert of rigid foam material disposed circumferentially within said bubble for cushioning said bubble against impact forces.

8. A dressing as set forth in claim 7 wherein said insert has an antimicrobial agent on a bottom surface for contacting a patient.

9. A dressing as set forth in claim 1 further comprising a removable release layer on said adhesive.

10. In combination, a Huber needle assembly having a housing, a needle for penetrating the skin of a patient and a tubing extending from said housing and being in communication with said needle; and a dressing for covering said housing, said dressing including a first section including a pad for engaging the skin of the patient and having an aperture for receiving said housing and a transparent bubble secured to said pad in alignment with said aperture for containing said housing therein and a transparent second section folded over said first section to cover said bubble and encase said tubing therebetween.

11. The combination of claim 10 wherein said second section has an adhesive on a periphery thereof for adherence to the skin of the patient.

12. The combination of claim 10 further comprising a closure for securing said second section to said first section to keep moisture from entering between said first section and said second section.

13. The combination of claim 12 wherein said closure includes a female component on one of said sections disposed in a U-shaped pattern and a male component on the other of said sections disposed in a U-shaped pattern for mating with said female component.

14. The combination of claim 10 wherein said pad includes a slit for passage of said tubing from said housing and said bubble has a slot aligned with said slit for passage of said tubing and said tubing is wound about said bubble.

15. The combination of claim 10 wherein said first section includes an insert of rigid foam material disposed circumferentially within said bubble for cushioning said bubble against impact forces.

16. The combination of claim 10 wherein said pad includes a layer of antimicrobial agent on a bottom surface surrounding said aperture for contacting the skin of the patient.

17. The combination of claim 10 wherein said Huber needle assembly includes a catheter on an end of said tubing and a closure clamp on said tubing, said catheter and said clamp being encased between said first section and said second section.

\* \* \* \* \*